United States Patent [19]

Lyman et al.

[11] Patent Number: 5,026,649
[45] Date of Patent: Jun. 25, 1991

[54] APPARATUS FOR GROWING TISSUE CULTURES IN VITRO

[75] Inventors: George Lyman, Cape Porpoise, Me.; Gregory Mathus, Concord; David Root, Lexington, both of Mass.

[73] Assignee: Costar Corporation, Cambridge, Mass.

[21] Appl. No.: 841,562

[22] Filed: Mar. 20, 1986

[51] Int. Cl.$^5$ .............................................. C12M 3/06
[52] U.S. Cl. .................................. 435/284; 435/297; 435/298; 422/101; 422/102
[58] Field of Search ............... 475/283, 284, 285, 286, 475/296, 297, 298, 299, 300, 301, 310; 422/101, 102; 210/321.84

[56] References Cited

U.S. PATENT DOCUMENTS

| | | | |
|---|---|---|---|
| 2,677,646 | 5/1954 | Lovell et al. | 435/297 X |
| 2,761,813 | 9/1956 | Goetz | 435/301 X |
| 3,275,528 | 9/1966 | Ainis | 435/284 X |
| 4,012,288 | 3/1977 | Lyman et al. | 435/298 X |
| 4,125,436 | 11/1978 | Liner | 435/287 |
| 4,246,339 | 1/1981 | Cole et al. | 422/102 X |
| 4,308,351 | 12/1981 | Leighton et al. | 435/284 |
| 4,603,105 | 7/1986 | Kaplan | 435/297 X |
| 4,608,342 | 8/1986 | Noes | 435/297 X |
| 4,670,396 | 6/1987 | Bear et al. | 435/310 X |
| 4,686,190 | 8/1987 | Cramer et al. | 435/285 X |

FOREIGN PATENT DOCUMENTS 2563232  10/1985  France ................. 435/298

Primary Examiner—David L. Lacey
Assistant Examiner—William H. Beisner
Attorney, Agent, or Firm—Wolf Greenfield & Sacks

[57] ABSTRACT

Apparatus for growing tissue cultures in vitro, which permits a concentration gradient of nutrients to develop through a permeable membrane to which a sample of tissue is attached. The permeable membrane is attached to the bottom end of a tubular support that in turn hangs by a flange connected to its upper end on the top of a well containing the nutrients. Typically, the well is part of a tissue culture cluster dish. The flange of the support positions the support and membrane centrally in the well so as to avoid capillary action in the space between the well and support. The configuration of the support and its cooperation with the lid of the cluster dish also prevents the support and membrane from floating in the nutrient solution in the well. Openings in the support provide access for a pipette to add and withdraw fluid from the space between the well and membrane support and from the space below the membrane.

40 Claims, 2 Drawing Sheets

APPARATUS FOR GROWING TISSUE CULTURES IN VITRO

INTRODUCTION

This invention relates to apparatus for growing tissue cultures in vitro and more particularly comprises a new and improved device for supporting tissue cultures in a fluid medium containing nutrients which promote the tissue culture growth. Until quite recently, in the conventional art of in vitro growth of mammalian tissues, tissue samples were affixed to the bottom of a tube or petri dish and bathed from above with a nutrient solution. In that mode, the tissue culture receives nutrients from above, i.e., from the side opposite the side attached to the tube or petri dish. That arrangement is contrary to the situation in the body where the plane of attachment of epithelial tissue to the underlying connective tissue is also the path of nutrient exchange. That prior art technique made the diagnosis and prediction of the malignant character of many epithelial tissue disorders very difficult.

More recently, perhaps dating from the publications of Dr. Joseph Leighton and the issuance of the Leighton et al. U.S. Pat. No. 4,308,351 dated Dec. 29, 1981 wherein many of his publications are listed, tissue cultures have been grown in vitro while receiving substantial quantities of nutrients for growth through a permeable membrane to which the tissue culture is attached. One widely used device is in the form of a molded plastic sleeve having a membrane secured across one end and on which the tissue culture is affixed within the sleeve. The sleeve has projecting feet at the end to which the membrane is attached, which serve to support the membrane-sleeve assembly in the well of a culture cluster dish. That device has several disadvantages. For example, the sleeve-membrane assembly is free to float in the fluid in the well, and therefore, the sleeve can move to a position closely adjacent the wall at one point about its diameter so as to permit capillary action which will cause the fluid outside the sleeve to wick up the sleeve and pass either into the sleeve or out of the well. Furthermore, the feet on the end of the sleeve to which the membrane is attached make it somewhat difficult to assemble the membrane on the sleeve. Yet another disadvantage of the prior art device is that it has no means by which the sleeve can be supported in an increased depth of nutrient solution in the well below the membrane. Rather, that depth is always limited to the height of the feet.

One important object of the present invention is to provide a membrane support which precisely positions the membrane-support assembly coaxially within the tissue culture cluster dish well in which it is mounted.

Another object of the present invention is to provide a support for membrane on which tissue culture is grown in vitro, which will prohibit capillary action between it and the container for the fluid medium in which the membrane-support assembly is placed.

Yet another object of the present invention is to provide a membrane-support assembly which allows a pipette to be inserted between the support and cluster dish well in which it is placed without disturbing or removing the assembly so that fluid may be introduced to or removed from the space between the support and well and beneath the membrane.

Yet another object of the present invention is to provide a membrane-support assembly which will so position the culture cluster dish lid so as to achieve a controlled evaporation rate for the fluid in the wells of the dish.

To accomplish these and other objects, the present invention includes a flat permeable membrane which is attached to one end of an essentially tubular support. The other end of the tubular support includes an outwardly extending flange which in turn carries a rim that can hang upon the upper end of a well in a tissue culture cluster dish. The flange centers the support in the well and prevents it from shifting laterally in the well. Therefore, the circular generally cylindrical wall of the support will not move close to the inner surface of the well wall in which it is placed so as to cause capillary action of the fluid in the well. The generally cylindrical side wall of the support is provided with a number of openings which allow a pipette to be inserted into the space between the support and well wall so that the pipette may reach the bottom of the well and introduce or remove medium from beneath the membrane and about the sides of the support. Knobs are provided on the upper surface of the rim which are adapted to engage the top wall of the lid of the tissue culture cluster dish so as to provide communication between the atmosphere and the interior of the support to control the evaporation rate of the fluid.

The membrane-support assembly is sized to be used with a cluster dish having wells of a specific size so as to provide the proper clearance about the support and engage the top end of the well. The membrane-support assembly may be made in different sizes so as to be used with different sizes of cluster dishes.

These and other objects and features of the present invention will be better understood and appreciated from the following detailed description of one embodiment thereof, selected for purposes of illustration and shown in the accompanying drawings.

BRIEF FIGURE DESCRIPTION

DETAILED DESCRIPTION

Figure 1:
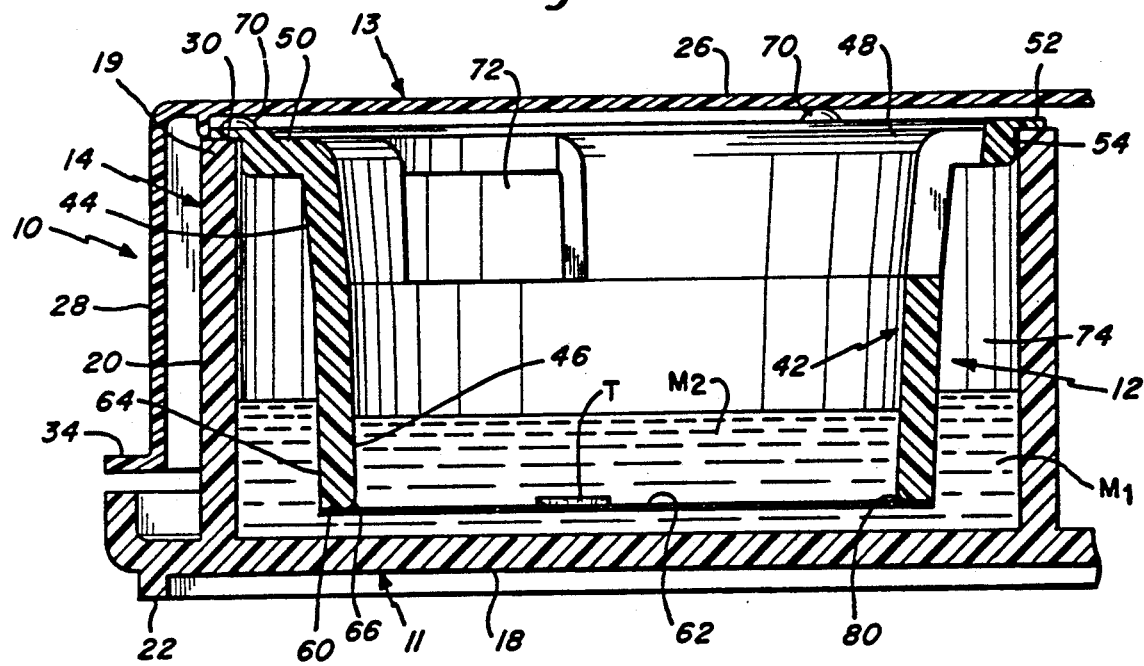
FIG. 1 is a cross-sectional view through one well of a tissue culture cluster dish and a membrane-support assembly constructed in accordance with the present invention and showing a tissue sample on the membrane.

The apparatus for growing tissue cultures in vitro shown in FIGS. 1 and 2 includes a tissue culture cluster dish 10 and a membrane-support assembly 12 which are described in detail below.

The tissue culture dish 10 is only partially illustrated in the drawings but is shown in detail in U.S. Pat. No. 4,495,289 dated Jan. 2, 1985 and assigned to Data Packaging Corporation, the assignee of the present invention. In the present application, only one well 14 of the cluster dish is shown, and it is to be appreciated that the cluster dish may have six, twelve, twenty-four or some other number of wells selected for the particular purpose for which the apparatus is used. Of course, each of the wells of the dish may contain a separate membrane-support assembly. As each of the other wells is identical to the well shown and each is used independently of the other, but a single well is illustrated.

The cluster dish 10 has a base 11 and lid 13. The base has a number of wells 14 each closed at the bottom by wall 18 and open at the top end 19. The side wall 20 of each well 14 is generally cylindrical and may include a slight draft which facilitates removal of the base from the mold in which it is formed. The base also includes a downwardly extending peripheral rib 22 on the lower side of its bottom wall 18 that supports the base on any working surface on which it is placed with the bottom wall 18 elevated above the working surface. The base 10 typically is transparent and may be molded of polyvinylchloride.

Lid 13 which may be molded of the same material as the base 10 has a top wall 26 and a surrounding depending skirt 28. When positioned on the base without anything projecting upwardly from the wells, the lid top wall 26 is spaced above the top edges 30 of the wells so as not to seal the open top ends 19 of the wells. The lid may be supported in that position by protrusions (not shown) on the base which engage the lower flange 34 of the lid skirt 28.

While in the foregoing paragraphs, the details of the cluster dish illustrated are described, it is to be appreciated that the details of the dish do not from part of the present invention, and the permeable membrane and its support may be sized to fit and be used with other cluster dishes.

The membrane-support assembly 12 of this invention includes an essentially tubular support 42 having an upper portion 44 and lower portion 46. The upper portion 44 is open at the top 48 and carries an outwardly extending flange 50 which serves to position the support in the well 14 of the culture dish.

Flange 50 carries a rim 52 that extends radially outwardly from the upper edge of the flange. The flange and rim together form a shoulder 54 that precisely positions the support 42 in well 14. The outer diameter of shoulder 54 is very slightly less than the inner diameter of the cylindrical wall 20 of well 14 at the top while the rim 52 exceeds the inner diameter of the inner surface of wall 20 and therefore rests upon the top edge 30 of the wall when the support is positioned in the well. This arrangement is clearly shown in FIGS. 1 and 2. With the support 42 in the position shown, it is evident that the support has little or no freedom to move laterally in the well 14. Similarly, the rim 52 prevents the support 42 from dropping to the bottom wall 18 of the well.

The lower portion 46 of the support has a flat bottom end 60 to which the membrane 62 of the assembly is attached. Typically, the membrane 62 is attached to the end 60 by either heat sealing or solvent bonding the two together. The periphery of the membrane 62 is trimmed flush with the outer surface 64 of the lower portion 46 of the support. It will be noted in FIG. 5 that a radius 66 is provided at the inner edge of bottom end 60 so as to prevent tearing of the membrane when the support and membrane are secured together. The membrane may be made of any suitable material including perforated inert film, hydrated gel or a layered combination wherein the latter is supported by the former.

Figure 5:
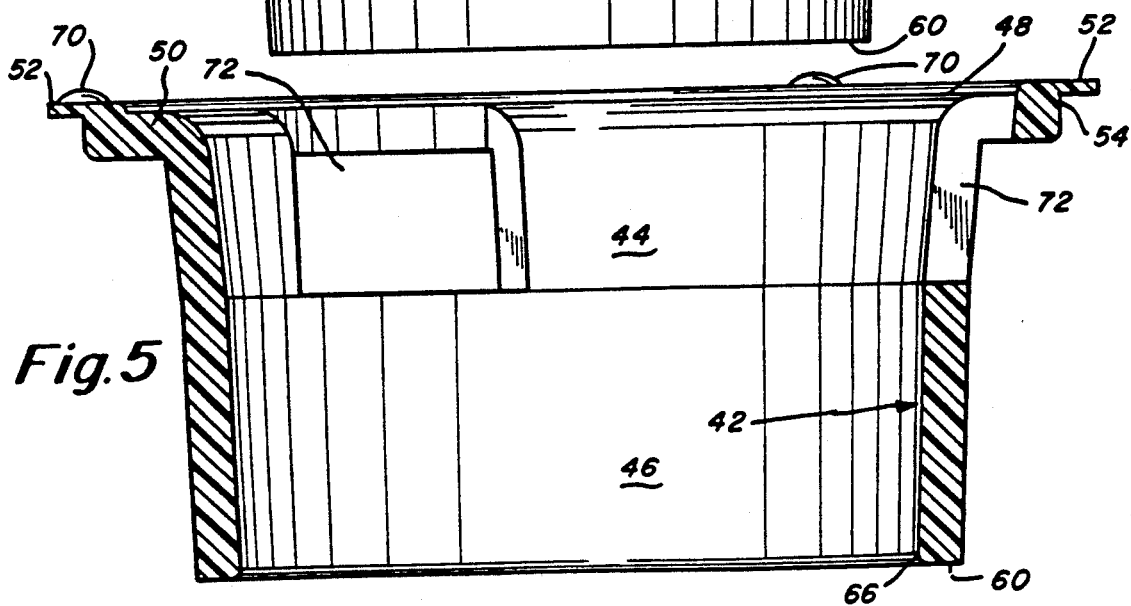
FIG. 5 is a cross-sectional view of the support taken along section line 5—5 in FIG. 3.

It will also be noted in FIG. 5 that the lower portion 46 of the support is provided with a slight draft, typically 2°, to facilitate the molding of the support. The upper portion 44 of the support is provided with a greater draft (6° is suggested). This 6° draft also assists in the molding operation by reducing the mold wear.

Figure 3:
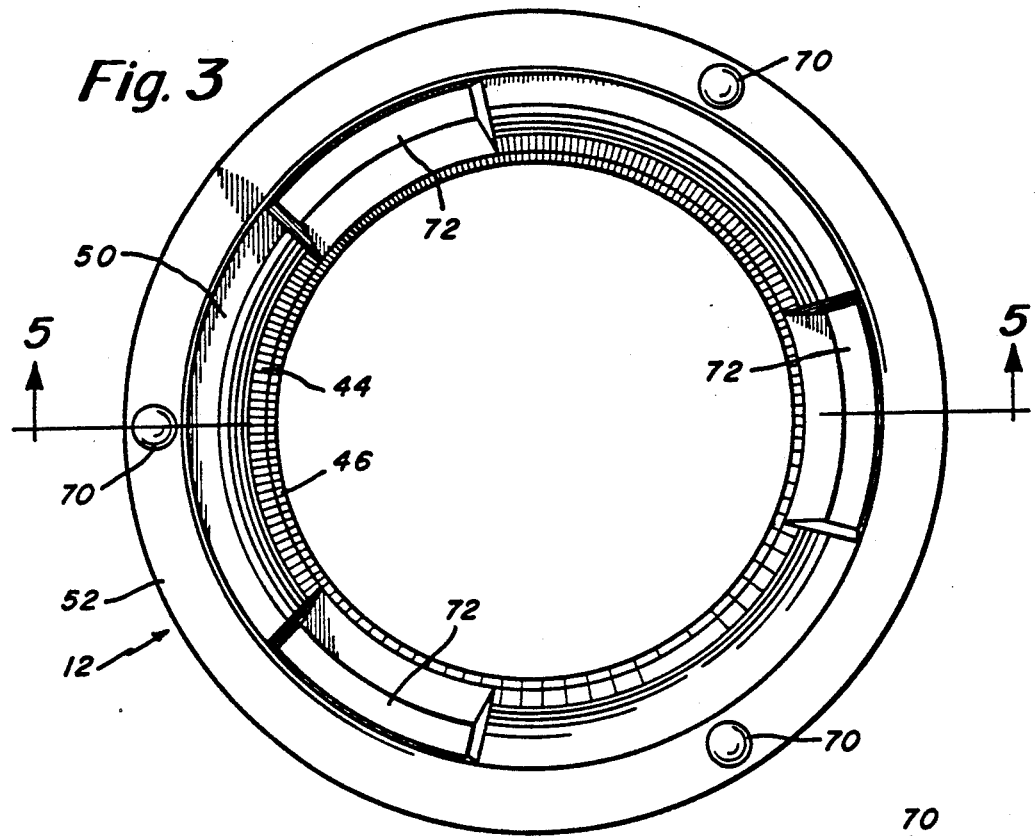
FIG. 3 is a plan view of the membrane support shown in FIGS. 1 and 2.
Figure 4:
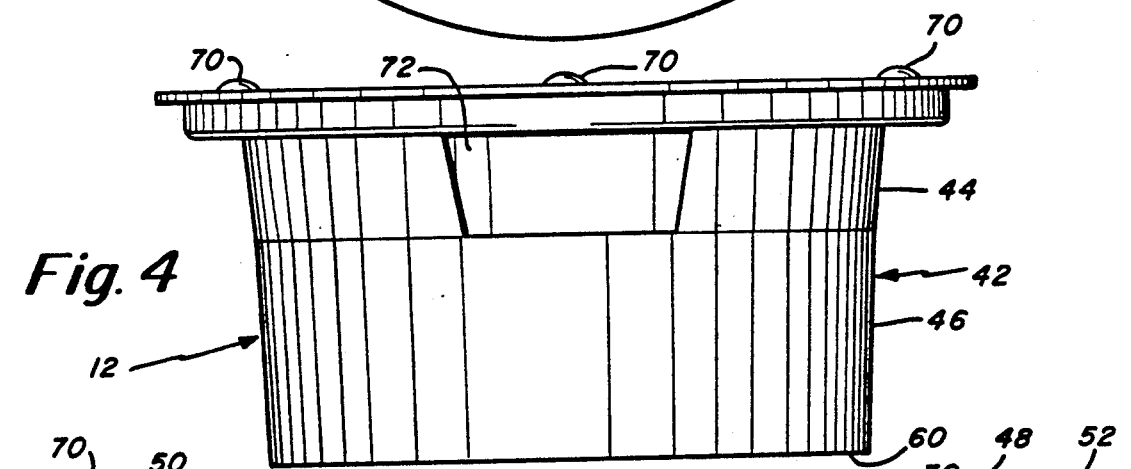
FIG. 4 is a side view of the support.

The rim 52 on flange 50 of support 42 carries a plurality of spaced knobs 70 that are intended to engage the bottom surface of top wall 26 of lid 13 of the cluster dish 10 so as to provide communication between the interior of well 14 (within and without membrane-support assembly 12) and the atmosphere. The spaced knobs 70, three of which are shown in FIG. 3, provide a controlled evaporation rate of the fluid in the well.

Three relatively large openings 72 are formed in the upper portion 44 of the support 12 spaced equidistantly about its circumference. The openings 72 extend into the flange 50. The function of the openings 72 is illustrated in FIG. 2 wherein a pipette tip T is shown to extend through one opening 72 to a position immediately adjacent the bottom wall 18 of the well 14. Thus, the openings 72 provide access to the annular space 74 between support 42 and well wall 20 and to the region below the membrane 62 so that medium may be introduced to or removed from those locations without disturbing or in any way removing the support from the well. The membrane-support assembly, however, can be lifted from the well 14 at any time merely by removing the lid 13.

In FIG. 1 a tissue culture sample T is shown secured to the upper surface of the membrane 62. A nutrient solution $M_1$ is shown to partially fill the annular space 74 in well 14 and the space below the membrane 62 that comprises one compartment. Depending upon the particular test or experiment being conducted, the same or a different solution $M_2$ may be disposed within the support 42 that comprises a second compartment and in contact with the tissue sample T and the upper surface of the membrane 62. The fill height of the separate solutions $M_1$ and $M_2$ in the annular space 74 and within the support 42 (the separate compartments) may or may not be the same.

Figure 2:
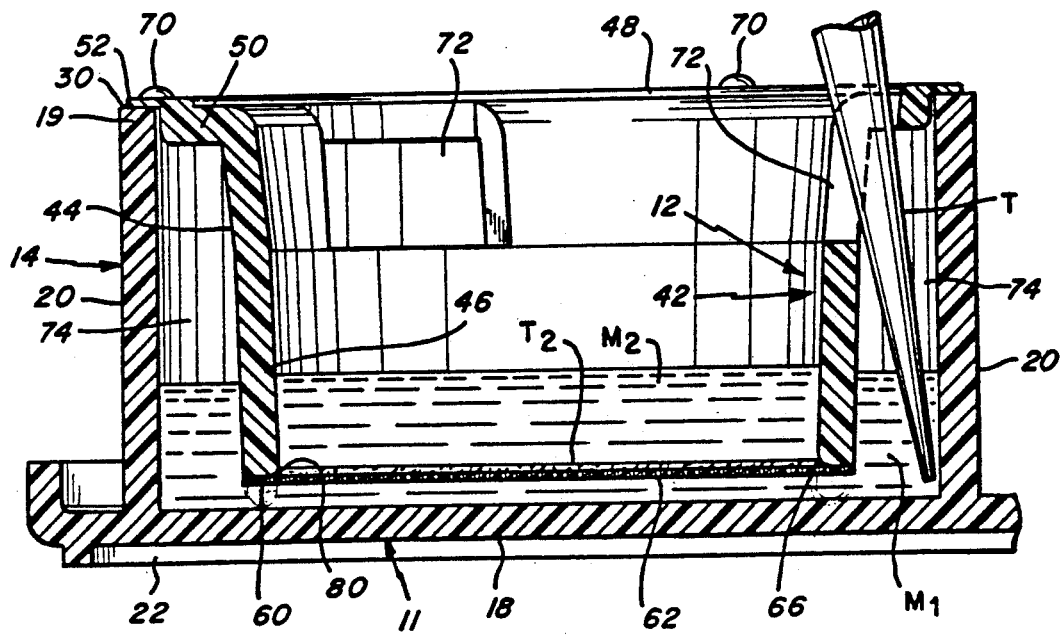
FIG. 2 is a cross-sectional view similar to FIG. 1 with the lid removed from the tissue culture cluster dish and showing how a pipette may be inserted into the space between the support and the well so as to add or remove fluid and further showing the tissue culture grown so as to cover the membrane.

In order to promote the growth of a monolayer of cells on the upper surface of the membrane within the support 42 as suggested in FIG. 2, the support 42 and the membrane may be treated by corona discharge or other technique so as to reduce surface tension of the surfaces. When so treated the tissue sample T and the tissue culture cultivated in the system will attach firmly to the membrane and seal at the edges 80 of the membrane 62 where the membrane joins the radius 66 of lower end 60 of the support. In FIG. 2, a thin monolayer of tissue cells $T_2$ is suggested extending to the edges of the membrane.

During the growth of the tissue culture, the lid 26 of the culture plate is placed over the base as suggested in FIG. 1, and when desired the lid may be removed and a pipette inserted as shown in FIG. 2 to either remove or add medium to the space 74. The tissue culture will receive substantial portion of its nutrients required for growth through the permeable membrane 62. Thus, a very simple system is provided which achieves the several objects of the invention set forth above.

It will be appreciated that because the support 42 is set within the well 14 and spaced sufficiently from the well side wall 20, no capillary action will occur to cause the solution in the space 74 from wicking up the wall and entering the interior of the support through the openings 72 or spilling from the well 14. When the membrane-support assembly is positioned in the well, the lid 13 serves to hold the assembly in position within the well. Consequently, the assembly cannot float in the solution and cause the rim 52 to unseat. Furthermore, because the flange and rim 50 and 52 support the membrane-support assembly, the culture may be treated if desired in a deeper well than suggested so as to provide more solution beneath the membrane. While it is customary to position the membrane 62 approximately 1 mm above the bottom wall 18, if desired, a well of greater depth may be used so as to provide additional space between the member and the bottom wall 18.

It will be appreciated that the tissue sample T attached to the membrane receives nutrients by diffusion through the membrane 62 from the nutrient bath provided in the well 14. Additional nutrients may be received from the solution within the well media such nutrients can thus pass unassisted from one well to the other only through the membrane.

Having described this invention in detail, those skilled in the art will appreciate that numerous modifications may be made thereof without departing from its spirit. Therefore, it is not intended to limit the breadth of this present invention to the single embodiment illustrated and described. Rather, the scope of this invention is to be determined by the appended claims and their equivalents.

What is claimed is:

1. In combination with a culture cluster dish having a matrix of wells closed at the bottom and open at the top and having an interior surface, apparatus for growing tissue cultures in vitro comprising,
    a membrane support having top and bottom ends and a generally cylindrical side wall with an external diameter smaller than the internal diameter of the wells so that the support may be disposed within a well of the dish,
    an outwardly extending flange at the top end of the support engaging the top of the well in which it is disposed to position the bottom end of the support a fixed and predetermined distance from the bottom of the well for providing access for fluid in the well to contact the lower side of a membrane when attached to the bottom end of the support,
    a permeable membrane attached to the bottom end of the support and forming a growth surface on the bottom of the membrane support, said permeable membrane spaced a fixed distance from the bottom of the well when the flange engages the top of the well for supporting and growing a tissue culture on its top surface,
    the membrane support having means for engaging a wall of the well for centering the support in the well so that said side wall is spaced from the interior surface of the well a sufficient distance to prevent the flow by capillary action up the space between the wall and the interior surface, and
    openings of sufficient size in the side wall of the membrane support providing access to the well bottom and between the bottom portion of the side wall and the interior surface of the well for a pipette to introduce and withdraw fluid therefrom and for gas exchange between the fluid and atmosphere.

2. The combination as defined in claim 1 wherein said openings extend into the flange and provide access from the interior of the top end of the side wall to the exterior of the bottom end of the side wall.

3. The combination as defined in claim 1 wherein the flange has an upper surface and knobs on the upper surface for supporting a lid in spaced relation to the flange.

4. The combination as defined in claim 2 wherein the flange has an upper surface and knobs on the upper surface for supporting a lid in spaced relation to the flange.

5. The combination as defined in claim 1, wherein said engaging means is a recess in said flange.

6. The combination as defined in claim 5, wherein said recess has a horizontally oriented side engaging the top of the well and a vertically oriented side engaging the wall of the well.

7. The combination as defined in claim 1, wherein said engaging means is integrally formed with said flange.

8. Apparatus for use with a tissue culture cluster dish having a plurality of closed bottom wells in growing tissue cultures in vitro comprising,
    a tubular body having a side wall and top and bottom ends, said side wall having top and bottom portions,
    a permeable member secured to the bottom end of the body for supporting a tissue culture on the side of the membrane facing the body so that said culture is disposed within the body,
    means secured to the top end of the body for supporting the body within a cluster dish well so that the bottom end of the body is a preselected spaced distance from the closed bottom of the well and said body and membrane divide the well into separate compartments each capable of receiving media,
    the tubular body having means for engaging a wall of the cluster dish well for centering the body in the well,
    and an opening of sufficient size in the side wall of the body for providing access to the well bottom and between the bottom portion of the side wall and the interior surface of the well for a pipette to introduce and withdraw fluid therefrom and for gas exchange between the fluid and atmosphere.

9. Apparatus as defined in claim 8 wherein said means secured to the top of the body is an outwardly extending flange for engaging the top of a well.

10. Apparatus as defined in claim 9 wherein said flange has an upper surface and knobs are provided on the upper surface of the flange for supporting a lid in spaced relationship thereto.

11. Apparatus as defined in claim 8, wherein said engaging means is a recess in said means secured to the top of the body.

12. Apparatus as defined in claim 11, wherein said recess has a horizontally oriented side engaging the top of the well and a vertically oriented side engaging the wall of the well.

13. Apparatus as defined in claim 8, wherein said engaging means is integrally formed with said flange.

14. Apparatus for use in growing tissue cultures in vitro comprising,
    a cluster dish having a well with side and bottom walls for receiving media to a selected fill height, a tubular body in the well and having a side wall and top and bottom ends, said side wall having top and bottom portions, a permeable member secured to the bottom end of the body for supporting a tissue culture on the side of the membrane facing the body so that said culture is disposed within the body, means secured to the top end of the body for supporting the body within the well with the bottom end of the body a preselected spaced distance from the bottom wall of the well for enabling media in the well to contact the bottom surface of the membrane, the tubular body having means for engaging a wall of the well for centering the body in the well, and an opening of sufficient size in the side wall of the body for providing access to the well bottom and between the bottom portion of the side wall and the interior surface of the well for a pipette to introduce and withdraw fluid therefrom and for gas exchange between the fluid and atmosphere.

15. Apparatus as defined in claim 14, wherein said engaging means is a recess in said means secured to the top of the body.

16. Apparatus as defined in claim 15, wherein said recess has a horizontally oriented side engaging the top of the well and a vertically oriented side engaging the wall of the well.

17. Apparatus as defined in claim 14, wherein said engaging means is integrally formed with said flange.

18. Apparatus for growing tissue cultures in vitro and supplying nutrients thereto through the surface to which the culture is attached comprising, a cluster dish having a plurality of wells with sides and closed bottoms, a tubular support disposed in a well of the dish with its axis vertical and closed at its bottom end by a permeable membrane on the top surface of which the culture is to be grown, means on the support for engaging the top and a wall of the well for centering the support in the well and for carrying the support with the membrane spaced above the closed bottom of the well and with the tubular support spaced from the sides of the well, said support and membrane dividing the well into an inner compartment within the support and an outer compartment outside the support, each of said compartments being capable of receiving media which can pass unassisted from one to the other of the compartments only through the membrane, and openings of sufficient size in the support for providing access with a pipette to the bottom of the outer compartment from the top of the inner compartment.

19. Apparatus as defined in claim 18, wherein said means for engaging is a flange having a recess.

20. Apparatus as defined in claim 19, wherein said recess has a horizontally oriented side engaging the top of the well and a vertically oriented side engaging the wall of the well.

21. Apparatus as defined in claim 19, wherein said engaging means is integrally formed with said flange.

22. Apparatus for growing tissue cultures in vitro and supplying nutrients thereto through the surface to which the culture is attached comprising, a cluster dish having a plurality of wells with sides and closed bottoms for receiving media, a support disposed in a well of the dish and having a tubular side wall with an upper edge and a bottom end and closed at its bottom end by a permeable membrane on the top surface of which the culture is to be grown, hanging means connected to the tubular side wall for supporting the support from the top of the well with the tubular side wall spaced from the interior surface of the sides of the well a sufficient distance to prevent flow by capillary action up the spaces between the side wall and interior surface, and with the membrane spaced above the closed bottom of the well, said hanging means engaging a wall of the well for centering the support in the well, said tubular side wall and membrane dividing the well into an inner compartment within the tubular side wall and an outer compartment outside the tubular side wall and below the membrane so that any media in the outer compartment communicates with the inner compartments only through the membrane, and an opening of sufficient size in the support for providing access with a pipette to the bottom of the outer compartment from the top of the well.

23. Apparatus as defined in claim 22, wherein said hanging means has a recess formed therein with a horizontally oriented position for engaging the top of the well and a vertically oriented position for engaging the well wall.

24. Apparatus for growing tissue cultures in vitro and supplying nutrients thereto through the surface to which the culture is attached comprising, a cluster dish having a plurality of wells with sides and closed bottoms, a support disposed in a well of the dish and having upper and lower portions, said lower portion having an upper end and being closed at its bottom end by a permeable membrane on the top surface of which the culture is to be grown, said upper portion comprising hanging means engaging both a wall and top of the well for positioning the support spaced from the top of the well with the lower portion of the support spaced from the interior surface of the sides of the well a sufficient distance to prevent flow by capillary action up the spaces between the lower portion of the support and interior surface, with the membrane spaced above the closed bottom of the well, said lower portion and membrane dividing the well into an inner compartment within the tubular side wall and an outer compartment outside the tubular side wall and below the membrane so that any media in said compartments flows from one to the other only through the membrane, and an opening of sufficient size in the upper portion of the support for providing access with a pipette to the bottom of the outer compartment from the top of the well.

25. Apparatus as defined in claim 24, wherein said hanging means has a recess with a horizontally portion engaging the top of the well and a vertical position for engaging the well wall.

26. In combination with a culture cluster dish having a matrix of wells closed at the bottom and open at the top and having an interior surface, apparatus for growing tissue cultures in vitro comprising, a membrane support having top and bottom ends and a generally cylindrical side wall with an external diameter smaller than the internal diameter of the wells so that the support may be disposed within a well of the dish, an outwardly extending flange at the top end of the support engaging the top of the well in which it is disposed to position the bottom end of the support a fixed and predetermined distance from the bottom of the well for providing access for fluid in the well to contact the lower side of a membrane when attached to the bottom end of the support, a permeable membrane attached to the bottom end of the support and spaced a fixed distance from the bottom of the well growing a tissue culture on its top surface, said generally cylindrical side wall and membrane dividing the well in which it is placed into a first fluid compartment within the membrane support and above the membrane and a second compartment outside the membrane support and below the membrane but inside the well, and said side wall being spaced from the interior surface of the well a sufficient distance to prevent the flow by capillary action up the space between the wall and the interior surface, and openings of sufficient size in the side wall for providing access to the second compartment between the permeable membrane and well bottom and between the bottom portion of the side wall and the interior surface of the well for a pipette to introduce and withdrawn fluid therefrom and for gas exchange between the fluid and atmosphere.

27. The combination as defined in claim 26 wherein said openings extend into the flange and provide access from the interior of the top end of the side wall to the exterior of the bottom end of the side wall.

28. The combination as defined in claim 27 wherein the flange has an upper surface and knobs on the upper surface for supporting the lid in space relation to the flange.

29. The combination as defined in claims 1 or 26 further comprising means in the flange for providing a passage for controlled evaporation from the well when a lid is placed over the cluster dish.

30. The combination as defined in claim 29 wherein the flange has an upper surface and said means in the flange are knobs on the upper surface for supporting the lid in space relation to the flange.

31. A tissue culture device for use with a tissue culture cluster dish having a plurality of closed bottom wells in growing tissue cultures in vitro comprising, a tubular body having a side wall and top and bottom ends, said side wall having top and bottom portions, a permeable member secured to the bottom end of the body for supporting a tissue culture on the side of the membrane facing the body so that said culture is disposed within the body, means secured to the top end of the body for supporting the body within a cluster dish well so that the bottom end of the body is spaced a preselected distance from the closed bottom of the well, and an opening of sufficient size in the top portion of the side wall of the tubular body for providing access from the interior of the top portion to the exterior of the bottom portion of the side wall of the body for a pipette to introduce and withdraw fluid therefrom and for gas exchange between the fluid and atmosphere.

32. A device as defined in claim 31 wherein said means secured to the top of the body is an outwardly extending flange for engaging the top of a well.

33. A device as defined in claim 32 wherein knobs are provided on the upper surface of the flange for supporting a lid in space relationship thereto.

34. A device as defined in claim 32 wherein the opening extends into the flange.

35. Apparatus for use in growing tissue cultures in vitro comprising, a cluster dish having a well with side and bottom walls for receiving media to a selected fill height, a tubular body in the well and having a side wall and top and bottom ends, said side wall having top and bottom portions, a permeable member secured to the bottom end of the body for supporting a tissue culture on the side of the membrane facing the body so that said culture is disposed within the body, means secured to the top end of the body for supporting the body within a well with the bottom end of the body a preselected spaced distance from the bottom wall of the well for enabling media in the well to contact the bottom surface of the membrane, and an opening of sufficient size in the side wall of the body for providing access to the well bottom and between the bottom portion of the side wall and the interior surface of the well for a pipette to introduce and withdraw fluid therefrom and for gas exchange between the fluid and atmosphere.

36. Apparatus for growing tissue cultures in vitro and supplying nutrients thereto through the surface to which the culture is attached comprising, a cluster dish having a plurality of wells with sides and closed bottoms, a tubular support disposed in a well of the dish with its axis vertical and closed at its bottom end by a permeable membrane on the top surface of which the culture is to be grown, means on the support for engaging the top of the well for centering the support in the well and for carrying the support with the membrane spaced above the closed bottom of the well and with the tubular support spaced from the sides of the well, said support and membrane dividing the well into an inner compartment within the support and an outer compartment outside the support, each of said compartments being capable of receiving media which can pass unassisted from one to the other of the compartments only through the membrane, and an opening of sufficient size in the support for providing access with a pipette to the bottom of the outer compartment from the top of the inner compartment.

37. Apparatus for growing tissue cultures in vitro and supplying nutrients thereto through the surface to which the culture is attached comprising, a cluster dish having a plurality of wells with sides and closed bottoms for receiving media, a support disposed in a well of the dish and having a tubular side wall with an upper edge and a bottom end and closed at its bottom end by a permeable membrane on the top surface of which the culture is to be grown, hanging means connected to the tubular side wall supporting the support from the top of the well with the tubular side wall spaced from the interior surface of the sides of the well a sufficient distance to prevent flow by capillary action up the spaces between the side wall and surface, and with the membrane spaced above the closed bottom of the wall, said tubular side wall and membrane dividing the well into an inner compartment within the tubular side wall and an outer compartment outside the tubular side wall and below the membrane so that any media in the outer compartment will communicate with the inner compartment only through the membrane, and an opening of sufficient size in the support for providing access with a pipette to the bottom of the outer compartment from the top of the well.

38. Apparatus as defined in claim 37, wherein said hanging means has a recess formed therein with a horizontally oriented position for engaging the top of the well and a vertically oriented position for engaging the well wall.

39. Apparatus for growing tissue cultures in vitro and supplying nutrients thereto through the surface to which the culture is attached comprising, a cluster dish having a plurality of wells with sides and closed bottoms, a support disposed in a well of the dish and having upper and lower portions, said lower portion having an upper end and being closed at its bottom end by a permeable membrane on the top surface of which the culture is to be grown, said upper portion comprising hanging means engaging both a wall and top of the well for positioning the support spaced from the top of the well with the lower portion of the support spaced from the interior surface of the sides of the well a sufficient distance to prevent flow by capillary action up the space between the lower portion of the support and surface, with the membrane spaced above the closed bottom of the well, said lower portion and membrane dividing the well into an inner compartment within the tubular side wall and an outer compartment outside the tubular side wall and below the membrane so that any media in said compartments flows from one to the other only through the membrane, and an opening of sufficient size in the upper portion of the support for providing access with a pipette to the bottom of the outer compartment from the top of the well.

40. A tissue growth device for use with a tissue culture cluster dish having a plurality of closed bottom wells in growing tissue cultures in vitro comprising, a tubular body having a side wall and top and bottom ends, said side wall having top and bottom portions, a permeable member secured to the bottom end of the body for supporting a tissue culture on the side of the membrane facing the body so that said culture is disposed within the body, means secured to the top end of the body for supporting the body within a cluster dish well so that the bottom end of the body is spaced a preselected distance from the bottom of the well and said body and membrane divide the well into separate compartments each capable of receiving media, and an opening of sufficient size in the top portion of the side wall of the tubular body for providing access from the interior of the top portion to the exterior of the bottom portion of the side wall of the bodies for a pipette to introduce and withdraw fluid therefrom and for gas exchange between the fluid and atmosphere.

* * * * *